United States Patent

Roldan et al.

[11] 4,146,720
[45] Mar. 27, 1979

[54] N-AMINOETHYL-SUBSTITUTED-3-NITRONAPHTHALIMIDES

[75] Inventors: Cristobal M. Roldan; Miguel F. Brana; Jose M. C. Berlanga, all of Madrid, Spain

[73] Assignee: Laboratorios Made, S.A., Madrid, Spain

[21] Appl. No.: 834,299

[22] Filed: Sep. 19, 1977

Related U.S. Application Data

[63] Continuation-in-part of Ser. No. 735,985, Oct. 27, 1976, abandoned, which is a continuation of Ser. No. 492,443, Jul. 29, 1974, abandoned.

[51] Int. Cl.² .................. C07D 221/14; A61K 31/47
[52] U.S. Cl. ........................ 546/99; 424/258
[58] Field of Search ................. 260/28 N, 28 NH

[56] References Cited

U.S. PATENT DOCUMENTS

| | | | |
|---|---|---|---|
| 3,310,564 | 3/1967 | Kasai | 260/281 |
| 3,330,834 | 7/1967 | Senshu | 260/281 |
| 3,625,947 | 12/1971 | Noguchi | 260/281 |
| 3,935,227 | 1/1976 | Wade et al. | 260/281 N |

OTHER PUBLICATIONS

Penso et al., "Tissue Cultures in Biological Research" pp. 129–132 (Elsevier Pub. Co., 1963).
Willmer, Ed., "Cells and Tissues in Cu Hare", pp. 360–373, (Academic Press, 1966).
Rolden, Chem. Abs. 84, 180053k (1975).
Dasheuskii et al., Chem. Abs. 55, 449i (1961).
Zollinger et al., Chem. Abs. 44, 8341c (1950).
Lab. Mode, S.A. Chem. Abs. 83, 97063 (1975).

*Primary Examiner*—Mark L. Berch
*Attorney, Agent, or Firm*—Blanchard, Flynn, Thiel, Boutell & Tanis

[57] ABSTRACT

Compounds having the formula

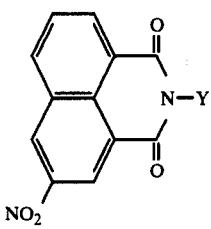

wherein Y is 2-dimethylaminoethyl, 2-diethylaminoethyl, 2-(N-pyrrolidino)ethyl or 2-(N-piperidino)ethyl. The compounds are prepared by reacting 3-nitronaphthalic acid, or corresponding anhydride, with the corresponding primary amine. The compounds possess cytostatic and raticide properties.

5 Claims, No Drawings

N-AMINOETHYL-SUBSTITUTED-3-NITRONAPHTHALIMIDES

CROSS REFERENCE TO RELATED APPLICATION

This application is a continuation-in-part of Ser. No. 735,985, filed Oct. 27, 1976, abandoned which in turn is a continuation of Ser. No. 492,443, filed July 29, 1974, abandoned.

The present invention relates to naphthalimides substituted at the nitrogen and in the three position, as well as a process for their preparation. The compounds show valuable cytostatic and raticide properties.

The compounds have the following general formula:

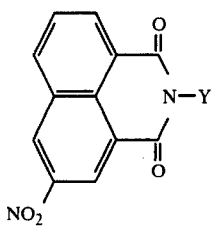

wherein Y is 2-dimethylaminoethyl, 2-diethylaminoethyl, 2-(N-pyrrolidino)ethyl or 2-(N-piperidino)ethyl.

The general synthesis method for these compounds is based on the reaction of the corresponding derivative of 3-nitronaphthalic acid, or its anhydride, with the corresponding primary amine in an appropriate solvent. The obtained product is then crystallized by means of an appropriate solvent.

Some examples that do not restrict the extent of the present invention are as follows:

EXAMPLE 1

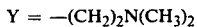

Y = —(CH$_2$)$_2$N(CH$_3$)$_2$

Into an Erlenmeyer flask of 250 ml capacity, provided with an electromagnetic stirrer, there is placed 7.29 g (0.03 mols) of 3-nitronaphthalic acid anhydride and 50 ml of ethanol. Add at once 2.64 g (0.03 mols) of N,N-dimethylethylenediamine. Stir the mixture for two hours. The solid formed is filtered and re-crystallized from a mixture of dimethylformamide-water in the usual form.

N-(2-dimethylaminoethyl)-3-nitronaphthalimide is a yellow solid with M.P. = 139°–40° C. (without correction).

Analysis: Calculated for C$_{16}$H$_{15}$N$_3$O$_4$: C = 61.33; H = 4.82; N = 13.41%. Found C = 61.35; H = 4.82; N = 13.41%

EXAMPLE 2

Y = —(CH$_2$)$_2$N(C$_2$H$_5$)$_2$

Into an Erlenmeyer flask of 250 ml capacity provided with an electromagnetic stirrer, there is placed 6.1 g (0.025 mols) of 3-nitrophthalic acid anhydride and 50 ml of ethanol. Add at once 2.9 g (0.025 mols) of N,N-diethylethylenediamine. Stir the mixture for two hours. The solid formed is filtered and re-crystallized from ethanol.

N-(2-diethylaminoethyl)-3-nitrophthalimide is a brown-yellow solid with M.P. = 120°–21° C. (without correction).

Analysis: Calculated for C$_{18}$H$_{19}$N$_3$O$_4$: C = 63.33; H = 5.61; N = 12.30%. Found C = 63.20; H = 5.47; N = 12.35%.

EXAMPLE 3

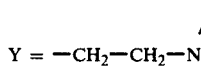

Into an Erlenmeyer flask of 250 ml capacity provided with an electromagnetic stirrer, there is placed 6.1 g (0.025 mols) of 3-nitronaphthalic acid anhydride and 50 ml of ethanol. Add at once 2.8 g (0.025 mols) of N-ethylpyrrolidine. Stir the mixture for two hours. The solid formed is filtered and re-crystallized from a mixture of ethanol-water in the usual form.

N-[2-(N-pyrrolidino)ethyl]-3-nitronaphthalimide is a brown-yellow solid with M.P. = 145°–46° C. (without correction).

Analysis: Calculated for C$_{18}$H$_{17}$N$_3$O$_4$: C = 63.70; H = 5.04; N = 12.38% Found C = 63.45; H = 5.10; N = 12.09%.

EXAMPLE 4

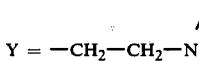

Into an Erlenmeyer flask of 250 ml capacity provided with an electromagnetic stirrer, there is placed 6.1 g (0.025 mols) of 3-nitronaphthalic acid anhydride and 50 ml of ethanol. Add at once 3.0 g (0.025 mols) of N-ethylpiperidine. Stir the mixture for two hours. The solid formed is filtered and re-crystallized from ethanol.

N-[2-(N-piperidino)ethyl]-3-nitronaphthalimide is a brown-yellow solid with M.P. 136°–37° C. (without correction).

Analysis: Calculated for C$_{19}$H$_{19}$N$_3$O$_4$: C = 64.57; H = 5.41; N = 11.89%. Found C = 64.75; H = 5.53; N = 11.69%.

The above-described compounds are:
1. N-[2-(N-piperidino)ethyl]-3-nitronaphthalimide
2. N-(2-diethylaminoethyl)-3-nitronaphthalimide
3. N-(2-dimethylaminoethyl)-3-nitronaphthalimide
4. N-[2-(N-pyrrolidino)ethyl]-3-nitronaphthalimide The fields of these four compounds are:
a. Very active cytostatic agents.
b. Raticide and muricide agents with a completely new structure and of great interest due to the very small amount of the drug necessary to obtain this effect. Moreover, they do not have a fulminant action, for which reason rats do not associate deaths with the bait.

Comparative experiments with substances possessing the same action in the above-mentioned field of use have been done.

A. AS CYTOSTATIC AGENTS

In the study of the cytostatic action, 6-mercaptopurine was taken as the comparative anti-neoplastic drug.

The study was done on He-La cells and on KB cells (H. Eagle, Proc. Soc. Exp. Biol., Med., 89, 362 (1955). The 50% inhibitory dose ($ID_{50}$) for each product included in this application was calculated using 6-mercaptopurine as the comparative drug. Moreover, a comparative study of the toxicity of our drugs with that of 6-mercaptopurine was done. In Table I, the values for $ID_{50}$, zero lethal dose ($LD_0$) or maximal permissible dose and the therapeutic index are shown. $LD_0$ and $LD_{50}$ are expressed in mg/mouse.

Table 1

| COMPOUND | $ID_{50}$ | $LD_0$ | $LD_{50}$ | Therapeutic index |
|---|---|---|---|---|
| 1) N-(2-N-piperidinoethyl)-3-nitronaphthalimide | 2 | 0.5 mg | 2 mg | 1 |
| 2) N-(2-diethylaminoethyl)-3-nitronaphthalimide | 3 | 0.15 mg | 2 mg | 0.66 |
| 3) N-(2-dimethylaminoethyl)-3-nitronaphthalimide | 0.15 | 0.2 mg | 0.30 mg | 2 |
| 4) N-(2-(N-pyrrolidino)ethyl-3-nitronaphthalimide | 0.3 | 0.2 mg | 0.38 mg | 1.26 |
| 6-mercaptopurine | 1 | 1 mg | 5 mg | 5 |

A series of tests has been carried out comparing the compounds of our invention with the corresponding 4-nitronaphthalimides, with respect to their cytotoxic activity on HeLa cells. The cytotoxic activity test was carried out in accordance with the procedure set forth in "R. I. Heral. Cancer Chemotherapy Report part III, Vol. III, No. 2".

HeLa cells are human cancer cells commonly used for investigating the cytotoxic activity of compounds. These HeLa cells are cultured by the single layer tissue culture technique on glass slides in the laboratories of the Spanish company, Laboratories Made, S.A., of Madrid, Spain, the assignee of this application.

In the tests, there was used an initial culture containing approximately 125000 HeLa cells per milliliter. The initial culture was dispersed with trypsin and was stirred to maintain the cells in suspension therein. Portions of equal volume of the suspension were placed in separate test tubes and to the test tubes were added the various compounds set forth below in various concentrations. There was employed as a standard for comparison, the compound 6-mercaptopurine, a known antineoplastic agent whose cytotoxic activity on HeLa cells is well known. As a control, there were also employed test tubes containing the suspension and to which no compound was added.

The contents of the test tubes were cultured at 37° C. for 72 hours. Then the contents of the various test tubes were examined by optical microscope to determine the approximate proportion of cells whose cellular growth was inhibited. Then, the protein content of each tube was determined by the Lowry method, as modified by Oyama and Eagle (Proc. Soc. Exptl. Biol. Med. 91, 305 (1956), and these values are compared with the corresponding values obtained in the control test tubes wherein no compound was added. Comparison of these measured protein values provides a further determination of the inhibition of cell growth caused by the test compounds. With the data obtained from the test tubes containing the same compound in various concentrations, a graph was prepared of concentration of compound versus inhibition of growth of HeLa cells. From this, there can be obtained the so-called $ID_{50}$ value, that is, the dose of the compound that inhibits HeLa cellular growth by 50%. This is then compared with the results for the comparison compound 6-mercaptopurine. For purposes of comparison, the $ID_{50}$ value of 6-mercaptopurine is assigned the value "1".

The test results were as follows:

| Compound Tested | $ID_{50}$ |
|---|---|
| N-[2-(N-piperidino)ethyl]-3-nitronaphthalimide (invention) | 2 |
| N-[2-(N-piperidino)ethyl]-4-nitronaphthalimide (control) | 5 |
| N-[2-diethylaminoethyl]-3-nitronaphthalimide (invention) | 3 |
| N-[2-diethylaminoethyl]-4-nitronaphthalimide (control) | 5.5 |
| N-[2-dimethylaminoethyl]-3-nitronaphthalimide (invention) | 0.15 |
| N-[2-dimethylaminoethyl]-4-nitronaphthalimide (control) | 3 |
| N-[2-(N-pyrrolidino)ethyl]-3-nitronaphthalimide (invention) | 0.30 |
| N-[2-(N-pyrrolidino)ethyl]-4-nitronaphthalimide (control) | 4 |
| 6-mercaptopurine | 1 |

The four compounds according to our invention have a greater cytotoxic activity than the corresponding four 4-nitro compounds used as controls, that is, the $ID_{50}$ value of the invention compounds is lower.

B. AS RATICIDE AGENTS

The four drugs were given to Swiss I.C.R. albino mice during 7 days. The administration was done by mixing the drugs with the usual mice food at concentrations of 1%, 0.5% and 0.1%. Two cribs were put in each cage: one with the usual mice food and the other containing food to which our drugs were added at the above mentioned concentrations. The food of both cribs was weighed daily in order to see if the animals could distinguish it. Warfarin (3-(α-acetonylbenzyl)-4-hydroxycoumarin) was used as the comparative substance.

The results obtained are shown in Table II.

Table II

| PRODUCT | Dose to be taken in seven days |
|---|---|
| Warfarin — | 35 mg/kg. |
| Compound 1 | 80 mg/kg. |
| Compound 2 | 13 mg/kg. |
| Compound 3 | 6.6 mg/kg. |
| Compound 4 | 6.6 mg/kg. |

It must be pointed out that mice death takes place within several days after the first ingestion of these products. Compounds 2, 3, 4 show a great superiority over Warfarin as raticide and muricide agents. Mice did not associate the deaths with food ingestion. They do not differentiate normal from lethal food. It is important to note that Compounds 2, 3 and 4 are more toxic and therefore they have a greater muricide action than Warfarin.

The embodiments of the invention in which an exclusive property or privilege is claimed are defined as follows:

1. A compound having the formula

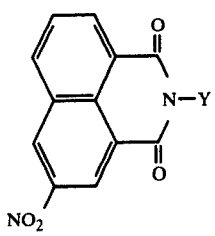
where Y is 2-dimethylaminoethyl, 2-diethylaminoethyl, 2-(N-pyrrolidino)ethyl or 2-(N-piperidino)ethyl.
2. A compound as claimed in claim 1 wherein Y is 2-dimethylaminoethyl.
3. A compound as claimed in claim 1 wherein Y is 2-diethylaminoethyl.
4. A compound as claimed in claim 1 wherein Y is 2-(N-pyrrolidino)ethyl.
5. A compound as claimed in claim 1 wherein Y is 2-(N-piperidino)ethyl.
* * * * *